United States Patent [19]

Gold-Aubert et al.

[11] Patent Number: 4,611,057
[45] Date of Patent: Sep. 9, 1986

[54] PROCESS FOR PREPARING PYRIMIDINETRIONE DERIVATIVES

[75] Inventors: Philippe Gold-Aubert; Diran Melkonian; Jindrich Vachta; Karel Valter, all of Geneva, Switzerland; Bernard Siegfried, Douvaine, France; Stéphane Hugentobler, Geneva, Switzerland

[73] Assignee: Sapos S.A., Geneva, Switzerland

[21] Appl. No.: 598,969

[22] Filed: Apr. 11, 1984

[30] Foreign Application Priority Data

Apr. 12, 1983 [GB] United Kingdom ............... 8309813

[51] Int. Cl.$^4$ .......................................... C07D 239/62
[52] U.S. Cl. ............................................. 544/301
[58] Field of Search ................................. 544/301

[56] References Cited

U.S. PATENT DOCUMENTS 3,075,983  1/1963  Gold-Aubert .................... 544/301

FOREIGN PATENT DOCUMENTS 873891  6/1971  Canada .

OTHER PUBLICATIONS

Gold-Aubert et al., *Helvetica Chimica Acta*, XLIV, pp. 105–113 (1960).

*Primary Examiner*—Donald G. Daus
*Assistant Examiner*—Stephen M. Kapner
*Attorney, Agent, or Firm*—Bacon & Thomas

[57] ABSTRACT

A process for the preparation of pyrimidinetrione derivatives of formula (I) is described

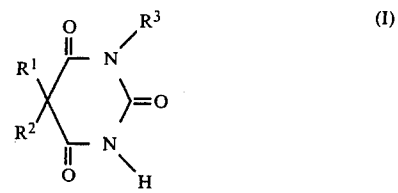

wherein $R^1$ and $R^2$, which may be the same or different, represent aliphatic, araliphatic or aryl groups, and $R^3$ represents a group of the formula —CH$_2$CH(OCONH$_2$)—CH$_2$OX wherein X is hydrogen or a C$_{1-5}$ alkyl group which comprises reacting approximately equimolar amounts of a monoalkali metal salt of a compound of formula (I), wherein $R^3$ is a hydrogen atom, with an alkylating agent $R^3$Hal wherein $R^3$ is as defined above and Hal represents a halogen atom, in the presence of at least 0.2 moles of an acid of formula (I) wherein $R^3$ is a hydrogen atom per mole of alkali metal salt. The yield is increased by up to 50% by this method. The process is of particular application to the preparation of febarbamate, 1-(3-$^n$butoxy-2-carbamoyloxypropyl)-5-ethyl-5-phenyl-(1H, 3H,5H)pyrimidine-2,4,6-trione. Also described is a method of treating geriatrics using febarbamate which has particular advantages in reducing irritability and antisocial behavior.

18 Claims, No Drawings

PROCESS FOR PREPARING PYRIMIDINETRIONE DERIVATIVES

This invention relates to a process for preparing pyrimidinetrione derivatives. It further relates to a method of improving the mental state of aggressive geriatrics to assist in making them more social by administering such pyrimidinetrione derivatives.

The compound, 1-(3-butoxy-2-carbamoyloxypropyl)-5-ethyl-5-phenyl-(1H,3H,5H) pyrimidine-2,4,6-trione known as and hereinafter called febarbamate has previously been prepared and described - see for example Helvetica Chimica Acta, XLIV, pp 105–113, (1960) and British Patent Specification No. 1,581,834. These publications also describe related compounds and their preparation. The method of preparation has generally involved the alkylation of phenobarbital (or other 5,5-disubstituted pyrimidinetrione) by forming the sodium salt of the appropriate malonyl urea and reacting it with an alkylating agent, e.g. a 1-halo-2-carbamoyloxy-3-n-butoxy propane, generally the chloro- compound. Such a process always provides a mixture of unchanged starting material, the N'-monosubstituted 5,5-disubstituted pyrimidinetrione derivative and the N,N'-disubstituted 5,5-disubstituted pyrimidinetrione derivative. Such derivatives are described in British Patent Specification No. 1,193,438. Various other reaction by-products are also obtained. The yield of e.g. febarbamate is generally around 50% or less.

We have now made a variation to the process which provides a significant increase in the yield of N-monosubstituted-5,5-disubstituted pyrimidinetrione.

According to one aspect of the invention, we provide a process for the preparation of a compound of formula (I)

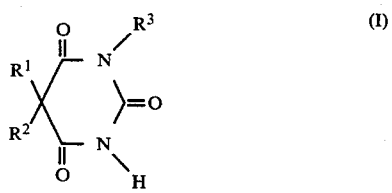

wherein $R^1$ and $R^2$, which may be the same or different, represent aliphatic, araliphatic or aryl groups, and $R^3$ represents a group of the formula —CH$_2$CH(OCONH$_2$)—CH$_2$OX wherein X is hydrogen or a C$_{1-5}$ alkyl group which comprises reacting approximately equimolar amounts of a monoalkali metal salt of a compound of formula (I) wherein $R^3$ is a hydrogen atom, with an alkylating agent $R^3$Hal wherein $R^3$ is as defined above and Hal represents a halogen atom, in the presence of at least 0.2 moles of an acid of formula (I) wherein $R^3$ is a hydrogen atom per mole of alkali metal salt. The compound of formula I formed may then be separated from undesirable by-products and/or unchanged starting material.

The groups $R^1$ and $R^2$ will preferably represent for example alkyl groups containing e.g. 1 to 5 carbon atoms, such as ethyl, propyl, or isopentyl; alkenyl groups containing e.g. 2 to 5 carbon atoms such as allyl; aralkyl groups wherein the alkyl moiety contains 1 to 4 carbon atoms, such as benzyl; and aryl groups, particularly carbocyclic aryl groups such as a phenyl group. X is preferably a C$_{2-4}$ alkyl group, such as $n$-butyl.

The acid employed will most desirably be in anhydrous form and is chosen so that it can readily be removed during subsequent washing of the product. It is also highly preferred to use a weak acid so as to avoid any side-reactions. The acid is generally the corresponding N-unsubstituted malonyl urea derivative, i.e. a compound of formula (I) wherein $R^3$ is a hydrogen atom.

Use of the N-unsubstituted barbituric acid compound itself as the acid occurs since this appears to act as a buffer in the reaction medium, hindering the second dissociation of the barbiturate compound and thus preventing disubstitution.

The group Hal in the alkylating agent will desirably be a chlorine atom, although bromine and iodine atoms could on occasions be used.

The alkali metal salt of the compound of formula (I) in which $R^3$ is hydrogen will most desirably be the sodium salt.

By including the acid in the reaction mixture, we have discovered that the amount of N-monosubstituted derivative formed rises significantly. In the case of febarbamate, it rises from 41% when no acid is used, to 51% when 0.172 moles of acid are used, to 59% when 0.25 moles of acid are used, to 62.5% when 0.5 moles of acid are used. This is an increase of more than 50%. The increase in yield occurs at the expense of the di-substituted derivative formed which drops, in the case of febarbamate/difebarbamate from about 39% when no acid used to about 23.4% when 0.5 moles of acid are used. There appears to be little benefit in adding more than 1 mole of acid per mole of monoalkali metal salt, and the yield of product appears to reach a maximum at from 0.5 to 0.6 moles of acid.

Use of anything other than equimolar quantities of the main reagents will desirably be avoided. This is because side-reactions may be encouraged, and because the cost rises rapidly if excess reagent is used.

The reaction will otherwise be carried out in a similar fashion to previous proposals. Thus, the reagents may be brought into intimate contact either by dissolution in a dry organic solvent, e.g. a hydrocarbon, amide, ether, sulphoxide or alcohol such as toluene, benzene, dimethylformamide, dioxan or ethanol or mixtures thereof and heated, or by fusion together and heated. It is preferred to carry out the fusion reaction at from 100° to 110° C. Reaction in solution will preferably be carried out just below the boiling point of the solvent. The monoalkali metal salt of the compound of formula (I) in which $R^3$ is hydrogen will desirably be added dropwise or in small portions to a mixture of the acid and the compound $R^3$.Hal at the start of the reaction in order to avoid sudden increases in temperature since the reaction is exothermic.

The amount of solvent present will desirably be just sufficient to dissolve and retain all the reagents in the liquid phase.

The N-monosubstituted compounds formed may be separated and isolated from the reaction mixture by a similar method to those previously proposed in the above-mentioned British Patent Specifications. This may be illustrated by the separation of the compound febarbamate which may be carried out as follows:

Separation:

Febarbamate itself is soluble in caustic alkali and the related disubstituted derivative is not. The reaction product mixture obtained, whether obtained as a viscous mass following fusion or as a solution may be extracted by the addition of from 5 to 10% by weight of an alkaline solution, as, for example, of an alkali metal hydroxide or the salt of an alkali metal with a weak acid e.g. a carbonate, bicarbonate or phosphate. The reagent of choice is sodium carbonate at a concentration e.g. of from 3 to 7.5%, since this is weak enough to avoid hydrolysing the carbamate group on the product.

The number of extractions that will be needed to isolate the febarbamate from the reaction product mixture depends to some extent on both the nature of the alkali employed and its concentration. Generally speaking, the first few extractions will remove phenobarbital itself. After this, a mixture of phenobarbital and febarbamate is obtained. It is then normal to obtain substantially pure febarbamate in the remaining extracts, the disubstituted compound or other disubstituted by-products remaining as an insoluble paste. The constituents of each extraction can be monitored by thin-layer chromatography (t.l.c.).

The carbonate extracts containing the febarbamate may be combined and precipitated by acidification, such as by using 10 to 15% hydrochloric acid. The pasty precipitate may be washed with water several times until the washings are approximately neutral.

The resulting solid may then be dissolved in a polar organic solvent, e.g. ethanol. Such a solution, on cooling, provides a mass of crystals having a melting point of from 98° to 107° C.

We have found this mass to contain diastereoisomeric forms of febarbamate. We have been able to resolve two diastereoisomers. The resolution of these may be followed using high performance liquid chromatography (h.p.l.c.), which achieves a separation and provides a ratio of the two diastereoisomeric forms but resolution may be achieved by fractional crystallisation from ethanol. The mixture may be dissolved in warm 95% by volume ethanol and allowed to stand, cooling slowly. By an appropriate combination of solvent and heating and cooling steps over suitable periods of time, α- and β- forms of febarbamate may be obtained.

Febarbamate itself has the formula

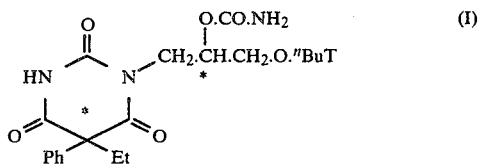

(I)

wherein Ph, Et and $^n$But stand for phenyl, ethyl and n-butyl groups respectively. The asterisks represent centres of asymmetry. The two forms which we have isolated have the n.m.r. spectrum (δ values) 0.92(t), 2.40(q), 9.4(s), 4.23(q), 3.89(q), 5.02(m), 3.49(d), 3.41(m), 1.48(m), 1.32(m), 0.90(t), 5.17(s), and 7.35(s) (α-form) and 0.92(t), 2.40(q), 9.5(s), 4.28(q), 3.83(q), 5.09(m), 3.48(d), 3.41(m), 1.48(m), 1.32(m), 0.89(t), 5.12(s) and 7.34(s) (β-form) and melting points of about 122.1° and 113.7° C. respectively. These contrast with a melting point of the mixture of both diastereoisomeric forms of from 99°–102° C. Such diastereoisomers are believed to be approximately 99% and 98% diastereoisomerically pure. By virtue of their purity, such isomers have particular therapeutic value, being substantially free of unwanted impurities, and the α- and β-forms of febarbamate comprise a further aspect of this invention as do pharmaceutical compositions comprising such α- and β-forms in association with a pharmaceutically acceptable carrier or excipient.

The general class of N-substituted pyrimidinetriones to which febarbamate belongs has good thymoanaleptic properties with no hypnotic or sedative properties and the compound itself enables "the vicious circle of perpetual intoxication and recourse to alcohol to avoid tremor to be broken."

We have further found that in addition to these generally described properties, febarbamate is extremely helpful in the general care of geriatric patients. Such patients are prone to fits of excitation, agitation and aggressivity and frequently become extremely antisocial. In a series of clinical tests, we have found the administration of febarbamate to have a significant improving effect upon the mental well-being of geriatrics. This is not a consequence of any mild sedative action. Indeed febarbamate appears to be superior in its action to the best compounds currently in clinical use for the treatment of irritable geriatrics.

In contrast to other psychotropic agents, febarbamate does not affect the personality and does not depress the patients' vigilance or other psychic reactions. This is an important quality of the product since elderly people are often quite psychically fragile. We have found febarbamate to produce a gentle and prolonged psychic stimulation which allows the patient to be more social, mentally alert and generally receptive.

Tests have been carried out using geriatric patients which show that the action of febarbamate is to be preferred either over the tranquilliser pipamperon (1-(p-fluorophenyl)-4-(4-piperidino-4-carbamoylpiperidino)-1-butanone) or the anticholinergic compound biperidene (α-5-norbornen-2-yl-α-phenyl-1-piperidinepropanol). In general it has been found that at a preferred dosage of three units of 150 mg each per day, numerous dysphoric states have notably improved without being able to detect any secondary effects. The thymism of the patients has, in particular, been improved to the extent that those who have previously been uncooperative have generally become much more amenable. Symptoms of excitability, aggressivity and agitation have been notably improved. The evaluation of such tests is carried out externally.

According to a further aspect of the invention therefore, we provide a method of treating old people to combat irritability and other antisocial behaviour which comprises administering to said people an amount of febarbamate effective to reduce irritability and antisocial behaviour without substantially impairing consciousness and/or resulting in sedation.

The febarbamate may be administered either on its own or in compositions. The compositions may take the form of tablets, coated tablets, capsules, lozenges, ampoules for injection or solutions.

The carriers or excipients in such compositions may, for example, be those conventional for such forms and may include starch, lactose, magnesium stearate, talc, gelatin, sterile pyrogen-free water, or suspending, emulsifying, dispersing, thickening or flavouring agents.

Dosage unit forms such as tablets, capsules or ampoules are preferred, and each unit contains 50 to 500 mg. of febarbamate, preferably 100 to 300 mg, e.g. 150 mg. A total daily dosage of from 150 mg to 1500 mg is suitable, for example from 350 to 1200 mg, administration of the drug desirably occurring three times per day.

It is preferred to administer the compound orally and compositions for oral administration are preferred.

The invention will now be more particularly described in the following Examples, which should not be construed as limiting. In the Examples, all temperatures are in °C. and h.p.l.c. refers to high performance liquid chromatography and is carried out on a Partisil 5 column, 25 cm long of 4 mm internal diameter, the mobile phase being pentane:diethylether: methanol (59:40:1) at a rate of 2 ml/min. U.V. detection occurs at 254 nm at a sensitivity of 0.1 a.u.f.s.

EXAMPLE 1

Preparation of febarbamate 5,5-Phenylethylmalonylurea (58 g) (0.25 mole) is mixed with 1-chloro-3-n-butoxypropan-2-ol carbamate (209.5 g) (1 mole). The mixture is warmed to 70° and sodium 5,5-phenylethylmalonyl urea (254 g) (1 mole) is added dropwise over 2 hours with stirring or agitation so that no sudden rise in temperature occurs and the reaction temperature is not allowed to exceed 100° to 110°. The mixture is retained at this temperature for six hours. A gummy mass which hardens on cooling is obtained.

The molten mass is then taken up in a water:toluene (1:1) mixture (600 ml) and the aqueous layer discarded. The toluenic solution is extracted with 5% by weight sodium carbonate solution (3×100 ml). With these first three carbonate extractions, sodium phenobarbital is obtained.

The toluenic solution is then successively washed with further 100 ml portions of 5% sodium carbonate solution. The first five extractions result in a mixture of sodium phenobarbital and sodium febarbamate, the yield of the former decreasing.

In general, after six extractions, only difebarbamate remains in the toluenic solution but extraction continues until h.p.l.c. analysis of a small sample of the solution shows no febarbamate peak.

The latter febarbamate - containing extracts are combined and treated with 15% hydrochloric acid. A pasty precipitate is obtained which can be washed with water until the washings are of pH about 7. The last traces of moisture may be removed by vacuum distillation, and minor quantities of by-products may be removed by recrystallisation from warm ethanol at 95°. The melting point of the febarbamate product was 98° to 104°. The yield was 59%.

In order to prepare febarbamate by reaction in solution, exactly the same quantities of reagents are used and are dissolved in 60% by weight of the mixture of the desired solvent. The mixture is heated at just below the boiling point of the solvent employed. The yield obtained is practically identical to that obtained in the equivalent fusion reaction.

By employing the procedure of Example 1, compounds of formula (I) in which $R^1$ and $R^2$ represent ethyl, allyl, n-propyl or phenyl groups and X is an ethyl, propyl or $^n$-butyl group have been prepared.

We claim:

1. A process for the preparation of a compound of formula (I)

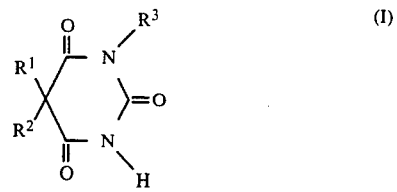

wherein $R^1$ and $R^2$, which may be the same or different, represent aliphatic, araliphatic or aryl groups, and $R^3$ represents a group of the formula —$CH_2CH(OCONH_2)CH_2OX$ wherein X is hydrogen or a $C_{1-5}$ alkyl group which comprises reacting approximately equimolar amounts of a monoalkali metal salt of a compound of formula (I) wherein $R^3$ is a hydrogen atom, with an alkylating agent $R^3Hal$ wherein $R^3$ is as defined above and Hal represents a halogen atom, in the presence of at least 0.2 moles of an acid of formula (I) wherein $R^3$ is a hydrogen atom per mole of alkali metal salt.

2. The process of claim 1 wherein the acid employed is anhydrous and is present in from 0.2 to 0.6 moles per mole of alkali metal salt.

3. The process of claim 1 wherein the alkali metal salt of the compound of formula (I) in which $R^3$ is hydrogen is the sodium salt, and the group Hal is a chlorine atom.

4. The process of claim 1 wherein reaction is carried out in the melt at a temperature of from 100° to 110° C.

5. The process of claim 1 wherein $R^1$ and $R^2$ each represents a $C_{1-5}$ alkyl group, $C_{2-5}$ alkenyl group, an aralkyl group in which the alkyl moiety contains 1-4 carbon atoms, or a carbocyclic aryl group.

6. The process of claim 5 wherein $R^1$ and $R^2$ are selected from ethyl, propyl, isopentyl, allyl, benzyl and phenyl groups.

7. The process of claim 5 wherein X represents a butyl group.

8. The process of claim 1 wherein the compound of formula (I) prepared is 1-(3-$^n$butoxy-2-carbamoyloxypropyl)-5-ethyl-5-phenyl(1H,3H,5H)pyrimidine-2,4,6-trione.

9. The process of claim 2 wherein the alkali metal salt of the compound of formula (I) in which $R^3$ is hydrogen is the sodium salt, and the group Hal is a chlorine atom.

10. The process of claim 2 wherein reaction is carried out in the melt at a temperature of from 100° to 110° C.

11. The process of claim 2 wherein $R^1$ and $R^2$ each represents a $C_{1-5}$ alkyl group, $C_{2-5}$ alkenyl group, an aralkyl group in which the alkyl moiety contains 1-4 carbon atoms, or a carbocyclic aryl group.

12. The process of claim 11 wherein $R^1$ and $R^2$ are selected from ethyl, propyl, isopentyl, allyl, benzyl and phenyl groups.

13. The process of claim 11 wherein X represents a butyl group.

14. The process of claim 12 wherein X represents a butyl group.

15. The process of claim 9 wherein the compound of formula (I) prepared is 1-(3-$^n$butoxy-2-carbamoyloxypropyl)-5-ethyl-5-phenyl(1H,3H,5H)pyrimidine-2,4,6-trione.

16. The process of claim 12 wherein the anhydrous acid is present in from 0.5 to 0.6 moles per mole of alkali metal salt.

17. The process of claim 16, wherein X represents a butyl group.

18. The process of claim 16, wherein the compound of formula (I) prepared is 1-(3-$^n$butoxy-2-carbamoyloxypropyl)-5-ethyl-5-phenyl(1H,3H,5H)pyrimidine-2,4,6-trione.

* * * * *